United States Patent
Kimura et al.

(10) Patent No.: US 8,749,964 B2
(45) Date of Patent: Jun. 10, 2014

(54) ULTRASONIC DIAGNOSIS APPARATUS

(75) Inventors: Masao Kimura, Kanagawa (JP); Masayoshi Hino, Ehime (JP); Tatsusi Chihara, Tokyo (JP); Yasuhiro Nakamura, Kanagawa (JP); Isamu Takagi, Ehime (JP); Erina Komatsu, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 317 days.

(21) Appl. No.: 13/122,480

(22) PCT Filed: Dec. 18, 2009

(86) PCT No.: PCT/JP2009/007016
§ 371 (c)(1),
(2), (4) Date: Apr. 4, 2011

(87) PCT Pub. No.: WO2010/073571
PCT Pub. Date: Jul. 1, 2010

(65) Prior Publication Data
US 2011/0235251 A1   Sep. 29, 2011

(30) Foreign Application Priority Data

Dec. 22, 2008   (JP) ................................ 2008-325932

(51) Int. Cl.
G06F 3/01 (2006.01)
G01S 7/52 (2006.01)
A61B 8/00 (2006.01)
G06F 1/16 (2006.01)
G06F 1/20 (2006.01)

(52) U.S. Cl.
CPC ............. *A61B 8/467* (2013.01); *G01S 7/52079* (2013.01); *A61B 8/463* (2013.01); *G06F 1/1643* (2013.01); *G06F 1/203* (2013.01); *G06F 1/1656* (2013.01); *G01S 7/52082* (2013.01); *A61B 8/462* (2013.01); *G06F 1/162* (2013.01); *Y10S 248/917* (2013.01)
USPC ........................ 361/679.26; 361/736; 248/917

(58) Field of Classification Search
CPC ........................... A61B 8/4427; G06F 1/1613

USPC ............. 361/679.01, 679.02, 679.08, 679.09, 361/679.21, 679.26, 679.27; 248/917–924; 600/437–472
See application file for complete search history.

(56) References Cited

U.S. PATENT DOCUMENTS 5,253,139 A   10/1993   Satou
5,644,469 A * 7/1997   Shioya et al. ............ 361/679.06
(Continued)

FOREIGN PATENT DOCUMENTS

JP   62-028864 A   2/1987
JP   03-109621 A   5/1991
(Continued)

OTHER PUBLICATIONS

International Search Report for PCT/JP2009/007016 dated Feb. 2, 2010.

*Primary Examiner* — Anthony Haughton
*Assistant Examiner* — Ingrid Wright
(74) *Attorney, Agent, or Firm* — Holtz, Holtz, Goodman & Chick, PC

(57) ABSTRACT

A technique which in a portable or laptop ultrasonic diagnosis apparatus, optimizes the position of a hinge mechanism for connecting a display section having a touch panel and a main body and the strength of the main body and also reduce the influence of noise between mutual sections, such as an ultrasonic image processing circuit board, a power source, a CPU board and the like, which are arranged inside the main body is disclosed. According to this technique, on a bottom surface of a bottom case 11 in the main body, a supporting section 12 for supporting a display section 20 is formed to stand upright and extend in a width direction, at a position that is dislocated to a front end F side from a rear end R of a main body 10. Also, a region A in which the ultrasonic image processing circuit board is arranged and regions B, C in which a power source unit and the CPU board are arranged, respectively, are partitioned by means of the supporting section 12.

6 Claims, 11 Drawing Sheets

(56) References Cited

U.S. PATENT DOCUMENTS

| | | |
|---|---|---|
| 2004/0105227 A1* | 6/2004 | Tanimoto et al. ............ 361/683 |
| 2005/0058877 A1 | 3/2005 | Fujita et al. |
| 2008/0125655 A1* | 5/2008 | Song et al. .................... 600/443 |

FOREIGN PATENT DOCUMENTS

| | | |
|---|---|---|
| JP | 3-144815 A | 6/1991 |
| JP | 04-213496 A | 8/1992 |
| JP | 04-284519 A | 10/1992 |
| JP | 4-136749 U | 12/1992 |
| JP | 05-242040 A | 9/1993 |
| JP | 06-051908 A | 2/1994 |
| JP | 06-230852 A | 8/1994 |
| JP | 06-324759 A | 11/1994 |
| JP | 10-005221 A | 1/1998 |
| JP | 11-508461 A | 7/1999 |
| JP | 11-316234 A | 11/1999 |
| JP | 2000-240636 A | 9/2000 |
| JP | 2005-108811 A | 4/2005 |
| JP | 2007-080011 A | 3/2007 |
| WO | 97/01768 A3 | 1/1997 |
| WO | 2006/103755 A1 | 10/2006 |
| WO | 2007/102213 A1 | 9/2007 |

* cited by examiner

ULTRASONIC DIAGNOSIS APPARATUS

TECHNICAL FIELD

The present invention relates to a foldable ultrasonic diagnosis apparatus in which a display section having a touch panel is opened/closed with respect to a main body.

BACKGROUND ART

As a display section having a touch panel, for example, there is a type disclosed in the following patent document 1. Also, as a foldable display section, for example, there is a type disclosed in the following patent document 2. Also, as a 2-shaft hinge mechanism of a foldable display section, for example, there is a type disclosed in the following patent document 3.

PRIOR ART DOCUMENT

Patent Document

Patent Document 1: Japanese Patent Application Publication No. H6-51908 (Abstract)
Patent Document 2: Japanese Patent Application Publication No. H4-284519 (Abstract)
Patent Document 3: Japanese Patent Application Publication No. 2000-240636 (Abstract)

By the way, the display section of the recent ultrasonic diagnosis apparatus is changing from CRT to a liquid crystal panel. Also, as the structure of the ultrasonic diagnosis apparatus, as shown in FIG. 12 and FIG. 13, it is possible to design a portable type or laptop type such as a note type personal computer (PC) and also design that a main body 1 and a liquid crystal display section 2 are foldable through an opening/closing shaft 3. By the way, FIG. 12 is a right side view showing a situation in which the liquid crystal display section 2 is closed, and FIG. 13 is a right side view showing a situation in which the liquid crystal display section 2 is opened. Moreover, the liquid crystal display section 2 is configured to have a touch panel so that an operation executed on the main body 1 side can be executed by touching the touch panel in the situation in which the liquid crystal display section 2 is opened, with a finger f.

However, in the ultrasonic diagnosis apparatus in which the display section 2 having the touch panel is foldable as mentioned above, the touch panel is pushed in the situation in which the liquid crystal display section 2 is opened from the main body 1. Thus, the strengths and arrangement positions of the respective members on the main body 1 side become problematic. In particular, as shown in FIG. 12 and FIG. 13, in a case that the position of the hinge mechanism (the opening/closing shaft 3) for connecting the display section 2 and the main body 1 is arranged at a rear end R of the main body 1, when the touch panel is pushed in the situation in which the liquid crystal display section 2 is opened and when the fastening force of the hinge mechanism is set stronger so as not to move the liquid crystal display section 2, there occurs a problem that a front end F side of the main body 1 is floated up (refer to an arrow in the center in FIG. 13). So, in order to solve this problem, for example, as indicated in the patent document 2, the position of the hinge mechanism 3 is considered to be slightly shifted to the front end F side from the rear end R of the main body 1. However, when the position of the hinge mechanism 3 is shifted from the rear end R of the main body 1 to the front end F side, unless the positions of the various parts, such as an ultrasonic image processing circuit board, a power source, a CPU board and the like, which are arranged inside the main body 1, are considered, there is a problem that the strength of the main body 1 is insufficient. Also, there is a problem that the influence of the noises from the power source and the CPU board on the ultrasonic image processing circuit board is increased. In particular, when the 2-shaft hinge mechanism is used as the hinge mechanism 3 and then the display section 2 can be opened/closed in an upper/lower direction with respect to the main body 1 and can be further rotated in a horizontal direction, the strength of the main body 1 becomes insufficient.

SUMMARY OF THE INVENTION

In view of the above problems, an object according to the present invention is to provide an ultrasonic diagnosis apparatus which in a configuration that a display section having a touch panel is opened/closed with respect to a main body, can optimize the position of a hinge mechanism for connecting the display section and the main body and the strength of the main body and can also reduce the noise, on an ultrasonic image processing circuit board, from the other boards such as a power source, a CPU board and the like, which are arranged inside the main body.

In particular, an object according to the present invention is to provide the ultrasonic diagnosis apparatus which in a case that the display section having the touch panel is connected through a 2-shaft hinge mechanism to the main body, can optimize the position of the 2-shaft hinge mechanism and the strength of the main body and can also reduce the noise.

In order to attain the above-mentioned objects, the present invention provides an ultrasonic diagnosis apparatus having:
an apparatus main body:
a display section having a touch panel, which can be opened/closed with respect to the apparatus main body;
a supporting section that is placed inside the apparatus main body and openably/closably supports the display section having the touch panel and extends up to a bottom surface of the apparatus main body, so as to divide an inner space of the apparatus main body into a plurality of regions which include a first region and a second region;
a first circuit section that is installed in the first region inside the apparatus main body and includes an image processing circuit board; and
a second circuit section that is installed in the second region inside the apparatus main body and includes a circuit board of a function different from the image process.

With the above configuration, in the configuration in which the display section having the touch panel is opened/closed with respect to the main body, it is possible to optimize the position of the hinge mechanism for connecting the display section and the main body and the strength of the main body, and it is possible to reduce the influence of the noise on the ultrasonic image processing circuit board, from the power source and the other boards such as the CPU board and the like, which are arranged inside the main body.

Also, the supporting section is formed to stand upright and extend in a width direction of the apparatus main body, on the bottom surface of the apparatus main body of a position that is dislocated to a front end side from a rear end of the apparatus main body, and configured to support the display section having the touch panel, and configured to arrange the image processing circuit board in the region on a main body front end side from the supporting section and also arrange a CPU board and a power source unit in the region on a main body rear end side from the supporting section.

With this configuration, in the foldable ultrasonic diagnosis apparatus in which the display section having the touch panel is opened/closed with respect to the main body, the display section is supported at the position that is dislocated to the front end side from the rear end of the main body. Thus, when the touch panel is pushed in the situation in which the display section is opened, even if the fastening force of the hinge mechanism is set stronger so as not to move the display section, the front end side of the main body section can be protected from being floated up. Also, the region in which the ultrasonic image processing circuit board is arranged and the region in which the CPU board and the power source unit are arranged are partitioned by the supporting section that is formed to stand upright and extend in the width direction on the bottom surface of the main body. Thus, it is possible to reduce the influence of the noises from the CPU board and the power source unit on the ultrasonic image processing circuit board.

Also, the supporting section is configured to have: a vertical shaft serving as a rotation shaft that enables the display section having the touch panel to be rotated in a horizontal direction with respect to the apparatus main body; and a horizontal shaft serving as an opening/closing shaft that enables it to be opened/closed in an upper/lower direction. Also, the supporting section is configured to serve as a 2-shaft hinge mechanism that has the vertical shaft and the horizontal shaft.

With this configuration, when the display section having the touch panel is connected through the 2-shaft hinge mechanism to the main body, it is possible to optimize the position of the 2-shaft hinge mechanism and the strength of the main body, and it is possible to reduce the influence of the noise.

According to the present invention, in the configuration in which the display section having the touch panel is opened/closed with respect to the main body, it is possible to optimize the position of the hinge mechanism for connecting the display section and the main body and the strength of the main body, and it is possible to reduce the influence of the noise from the various parts such as the power source, the CPU board and the like on the ultrasonic image processing circuit board arranged inside the main body. Also, when the display section having the touch panel is connected through the 2-shaft hinge mechanism to the main body, it is possible to optimize the position of the 2-shaft hinge mechanism and the strength of the main body, and it is possible to reduce the influence of the noise of the circuit or mutual circuit boards.

DESCRIPTION OF EMBODIMENTS

First Embodiment

Figure 1A:
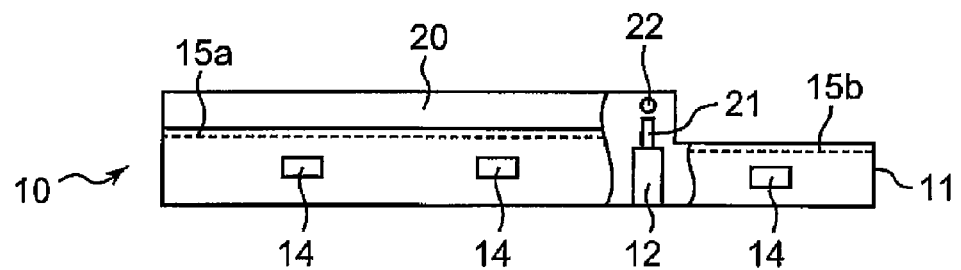
FIG. 1A is a right side view of a first embodiment of an ultrasonic diagnosis apparatus according to the present invention.
Figure 1B:
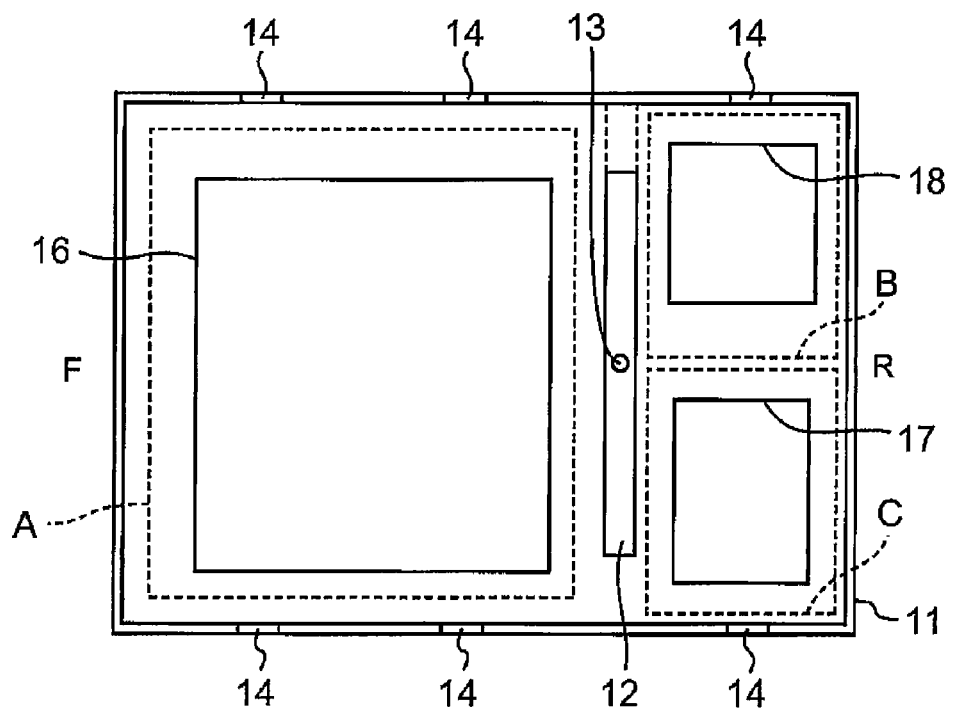
FIG. 1B is a plan view showing a bottom case configuring a main body of the ultrasonic diagnosis apparatus in FIG. 1A.

The embodiment according to the present invention will be described below with reference to the drawings. FIG. 1A is the right side view of the first embodiment of the ultrasonic diagnosis apparatus according to the present invention, and FIG. 1B is the plan view showing a bottom case 11 configuring a box-shaped apparatus main body 10 of a portable or laptop ultrasonic diagnosis apparatus in the embodiment shown in FIG. 1A. In this application, the above apparatus main body is also merely referred to as the main body. Also, FIG. 2 is the exploded perspective view showing the first embodiment of the ultrasonic diagnosis apparatus shown in FIG. 1A and FIG. 1B.

Figure 2:
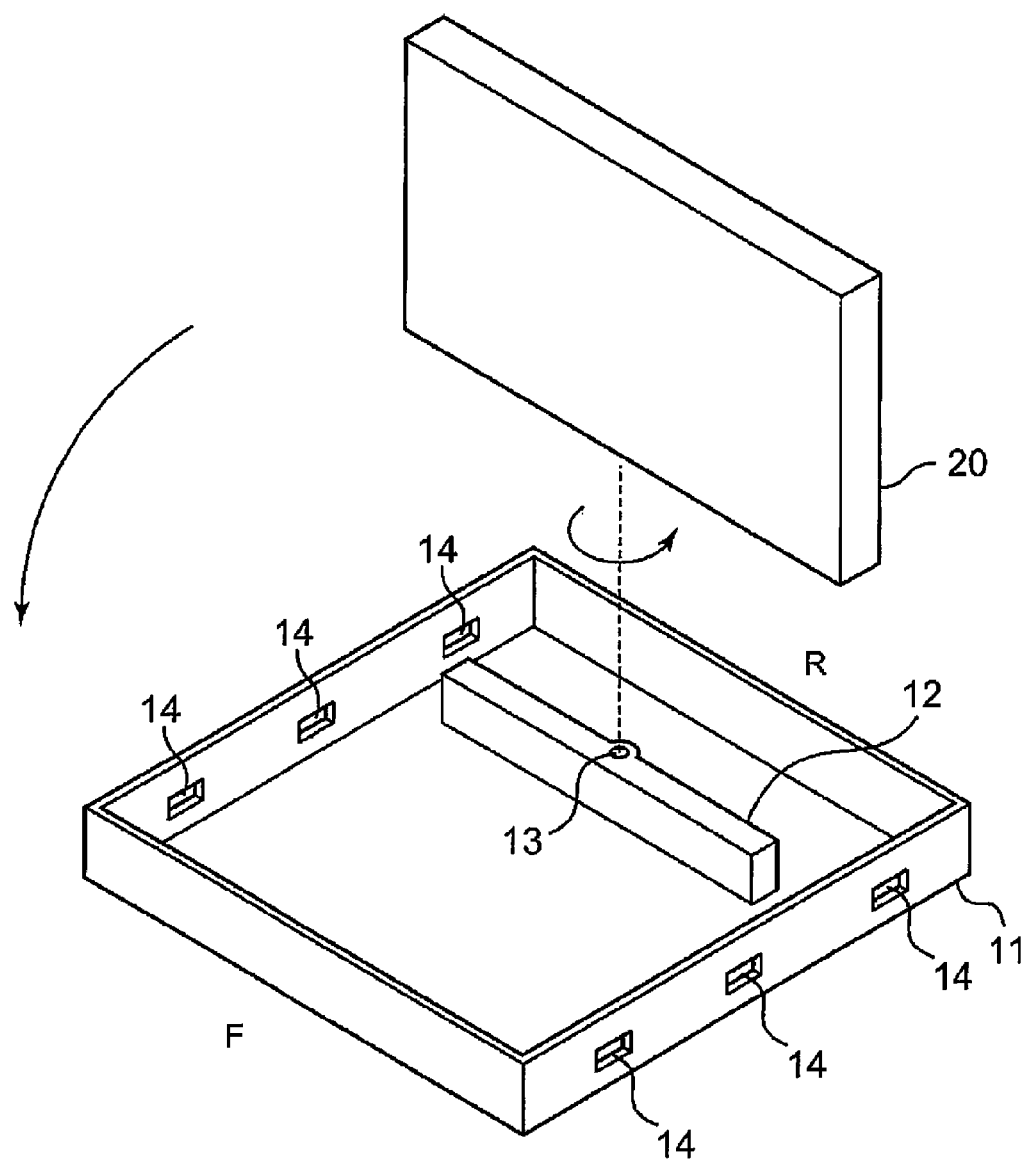
FIG. 2 is an exploded perspective view showing the ultrasonic diagnosis apparatus in FIG. 1A and FIG. 1B.

In FIG. 1 and FIG. 2, a display section 20 having a touch panel is rotated at a position at which its lower end is dislocated by a predetermined distance to a front end F side from a rear end R of the main body 10, with respect to a main body 10, and consequently, its upper end is opened/closed in an upper/lower direction with respect to the main body 10, and its whole is supported rotatably in a horizontal direction. On the bottom surface of a bottom case 11, a supporting section 12 for supporting the display section 20 is formed to stand upright and extend in a width direction. In the center in the longitudinal direction of the supporting section 12, an engagement hole 13 with which a vertical shaft 21 is engaged is formed. On the vertical shaft 21, a horizontal shaft 22 is supported, and the horizontal shaft 22 is connected to the lower end of the display section 20. The display section 20 can be rotated in the horizontal direction with the vertical shaft 21 as a rotation axis, with respect to the main body 10 and can be also opened/closed in the upper/lower direction with the horizontal shaft 22 as an opening/closing axis, and the vertical shaft 21 and the horizontal shaft 22 configure the 2-shaft hinge mechanism. Also, on both sides of the main body 10, a plurality of openings 14 for radiating are formed. By the way, in an embodiment that will be described later, a part of the openings 14 can be used as an attachment for a connector and the like.

Also, as shown in FIG. 1B, a region A of the front end F side from the supporting section 12 in the bottom case 11 is a region in which an ultrasonic image processing circuit board 16 is arranged, and a power source unit 17 and a CPU board 18 are arranged in regions B, C of the rear end R side from the supporting section 12, respectively. Also, as shown in FIG. 1A, at a position which is on the bottom case 11 and to which the display section 20 is oppose, an operating section 15a is attached, and under the operating section 15a, the ultrasonic image processing circuit board 16 is attached (refer to FIG. 1B). Also, in the regions B, C that are on the bottom case 11, an upper case 15b is attached (refer to FIG. 1A).

According to such configuration, on the bottom surface of the bottom case 11, the supporting section 12 for supporting the display section 20 is formed to stand upright at a position that is dislocated to the front end F side from the rear end R of the main body 10 and to extend in the width direction of the main body 10. Thus, when the touch panel is pushed in the situation in which the display section 20 is opened, even if the fastening forces of the 2-shaft hinge mechanisms (21, 22) are set stronger so as not to move the display section 20, the front end F side of the main body 1 can be protected from being floated up. Also, the region A in which the ultrasonic image processing circuit board 16 is arranged and the region including the regions B, C in which the power source unit 17 and the CPU board 18 are arranged, respectively, are divided into two by the supporting section 12 that is formed to stand upright and extend in the width direction, on the bottom surface of the bottom case 11. Thus, it is possible to reduce the influence of the noise, which is caused by the propagation of electromagnetic waves from the CPU board 18 and the power source unit 17 and the like, on the ultrasonic image processing circuit board 16. By the way, although not placed on the ultrasonic image processing circuit board 16, when there is a circuit configuration element closely related thereto, as the circuit section including the ultrasonic image processing circuit board 16 together with its portion, it is arranged in the region A. Similarly, although not placed on the CPU board 18, when there is a circuit configuration element closely related thereto, as the circuit section including the CPU board 18 together with its portion, it is arranged in the region B. Moreover, since an electromagnetic shield whose illustration is omitted is placed for each of the respective regions A, B and C, it is possible to further reduce the influence from the noise mixture caused by the mutual electromagnetic wave and the like. Also, the bottom case 11 is preferred to be made of the conductive material such as a synthetic resin with which metals and carbon particles are mixed, and the like. In this case, an idea in which the supporting section 12 is integrally molded by using the same material as the bottom case 11 is a preferable implementation. Also, when the supporting section 12 is separately placed without being integrally molded with the bottom case 11, the supporting section 12 is preferred to be made of the conductive material such as a synthetic resin with which metals and carbon particles are mixed, and the like.

Second Embodiment

Figure 3:
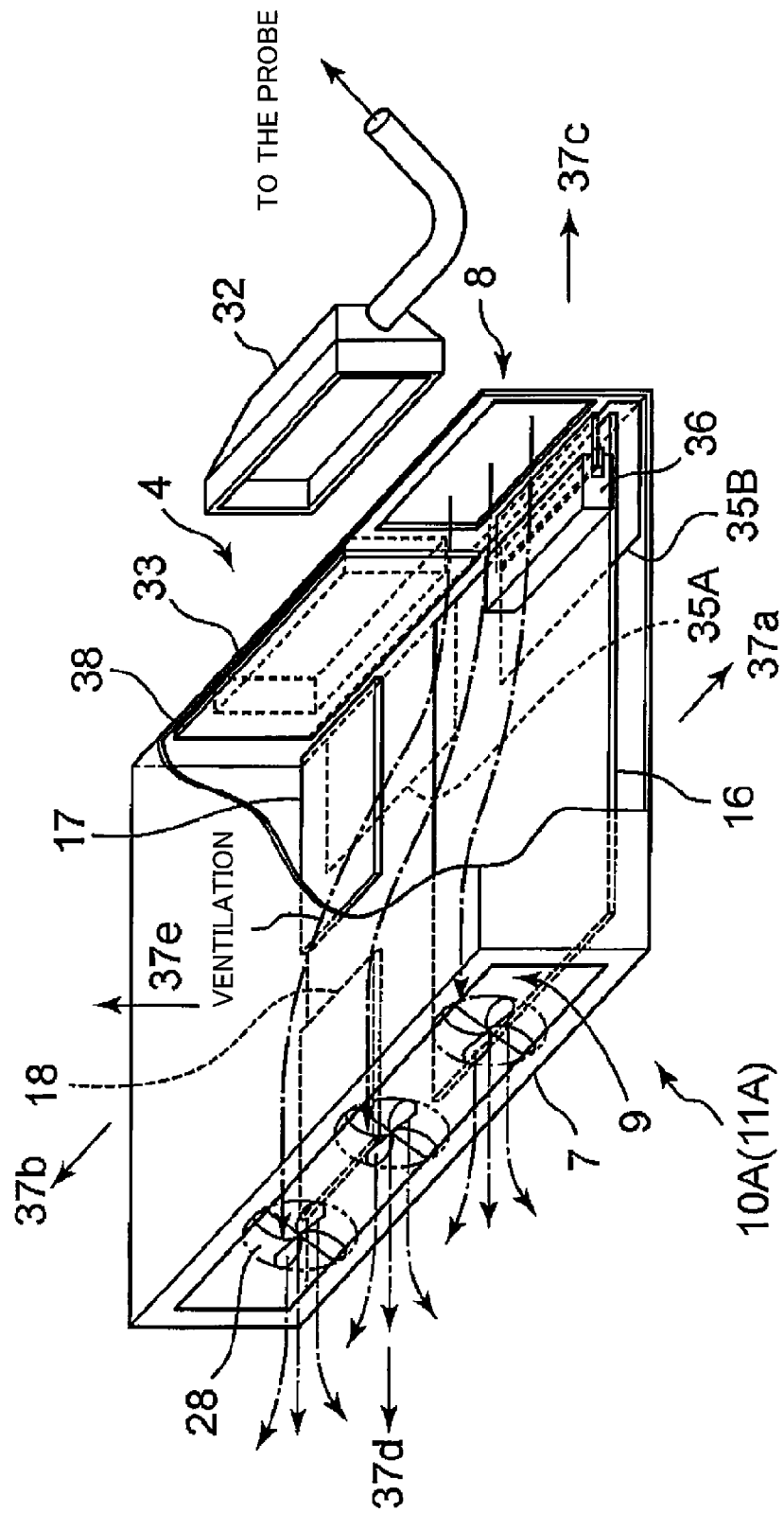
FIG. 3 is a perspective view showing a main body in a second embodiment of the ultrasonic diagnosis apparatus according to the present invention.

FIG. 3 shows the main body and its periphery in the second embodiment of the ultrasonic diagnosis apparatus according to the present invention. In a main body 10A in the second embodiment, the main body 10 in the first embodiment serves as the base. Then, the main body 10A is provided with a bottom case 11A and a portion covering its upper surface, similarly to the first embodiment. However, for convenience, the main body 10A and the bottom case 11A are shown without any discrimination. By the way, the correspondence relation between the second embodiment and the first embodiment will be described later. In the second embodiment, the supporting section 12 in the first embodiment is also placed. However, its illustration is omitted in FIG. 3. FIG. 3 shows a probe side probe connector 32 that is connected through a cable and the like to a probe (not shown), in order to transmit/receive an ultrasonic wave inside a living body. The main body 10A in the ultrasonic diagnosis apparatus is provided with: a main body side probe connector 33 for connecting the ultrasonic image processing circuit board 16 and the CPU board 18 to the probe side probe connector 32; an opening 4 for exposing the main body side probe connector 33 to the outside from the bottom case 11A, FPCs (Flexible Printed Circuits) 35A, 35B that are flexible printed circuits for the connection between the main body side probe connector 33 and the ultrasonic image processing circuit board 16 and the CPU board 18; an FPC connector 36 that is mounted on the ultrasonic image processing circuit board 16 for the connection to the FPC 35B; the bottom case 11A for housing those respective configuration elements; an opening 8 serving as an external air intake hole for thermal exhaustion that is located on the main body side probe connector 33 side on the side of the bottom case 11A; an opening 9 for thermal exhaustion that is located on the side opposite to the side in which the opening 8 of the bottom case 11A is located; and a plurality of cooling fans 28 for thermal exhaustion that are attached to the opening 9.

By the way, in the configuration of many FPCs, it is provided with: a flexible portion on which the pattern of copper foil is drawn; and a resin plate composed of a glass epoxy plate for reinforcing and supporting a terminal portion to connect this to the terminal of the mounted part by soldering and the like. In this embodiment, a resin plate 38 (second board) is placed on the portion to connect the main body side probe connector 33 of the FPC 35A. The resin plate 35B serving as the second board is placed in a vertical state as shown in FIG. 3, although the ultrasonic image processing circuit board 16 and the CPU board 18, which serve as the first board, are horizontally placed.

In detail, FIG. 3 is the view when it is viewed from the oblique direction of the front side, and an arrow 37a indicates the operator side (corresponds to the side indicated by F in FIG. 2 that shows the first embodiment) on the bottom case front side, and an arrow 37b indicates the bottom case rear side (corresponds to the side indicated by R in FIG. 2, and hereafter, this is merely referred to as a rear side 37b), and the main body side probe connector 33 is arranged on the surface of an arrow 37c side (hereafter, merely referred to as a right side 37c) serving as the operator right side. The cooling fan 28 for the thermal exhaustion is located on the surface of an arrow 37d side (hereafter, merely referred to as a left side 37d). This reason lies in a fact that, since the thermal exhaustion is hot air, the operator or a patient has a feeling of discomfort when receiving it. Thus, this is arranged on the left side 37d or the rear side 37b that are located away from the operator or patient. The display section composed of a liquid crystal panel for displaying a diagnosis image and the like is installed on a liquid crystal surface 37e on the main body 10A.

In the configuration of FIG. 3, the FPC 35B is arranged so as to creep on the inner bottom surface of the bottom case 11A and rises from below the ultrasonic image processing circuit board 16 and is connected to the FPC connector 36. Also, the FPC 35A rise from below, along the vertical right side 37c on which the main body side probe connector 33 in the bottom case 11A is placed, and this is supported by the resin plate 35B that also functions as a reinforcement plate.

Consequently, the opening 8 can be formed in the portion remaining on the right side 37c. When it is pulled from the short side of the resin plate as mentioned above, this is configured to avoid the right side 37c from being covered with the pulled FPC 35.

As mentioned above, according to the second embodiment, it has the configuration in which the FPC 35B is placed to pull the pattern from the long side of the main body side probe connector 33. With this configuration, the opening 8 whose size enables an efficient ventilation can be formed in the side (the right side 37c in the example of FIG. 3) of the bottom case 11A to which the main body side probe connector 33 is attached. Thus, the ventilation through the cooling fan 28 is improved, there by enabling the efficient thermal exhaustion. For this reason, the mounting density of the inner electric circuits can be made high, which can include the larger number of channels. Hence, it has an effect of being able to provide the portable ultrasonic diagnosis apparatus that attains the performance and image quality which are not inferior to a platform integration type.

Figure 4:
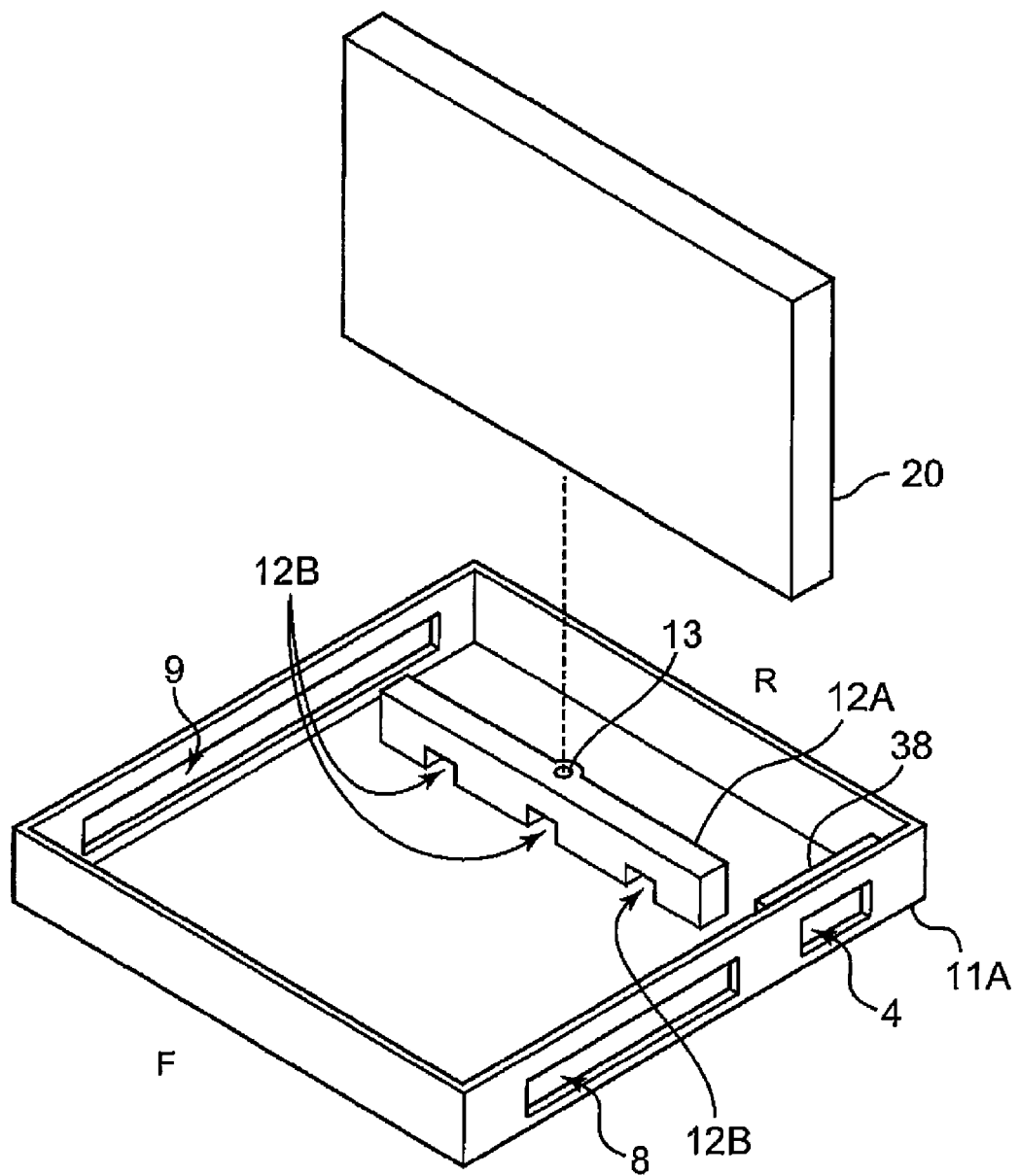
FIG. 4 is a perspective view showing a display section and a bottom case of a main body that configure the second embodiment shown in FIG. 3.

FIG. 4 is the perspective view of the second embodiment, which shows only the bottom case 11A and the display section 20 in FIG. 3. By the way, as shown in FIG. 4, a plurality of ventilation holes 12B are formed in a supporting section 12A. Although the plurality of cooling fans 28 shown in FIG. 3 are placed in the opening 9, the illustration of the cooling fan 28 is omitted in FIG. 4. Also, the illustrations of the ultrasonic image processing circuit board 16, the power source unit 17 and the CPU board 18, which are arranged in the regions A, B and C in FIG. 3, respectively, are omitted. When the cooling fans 28 are driven, the air outside the bottom case 11A is taken from the opening 8 and exhausted through the inner space of the bottom case from the opening 9 to the outside. At this time, inside the bottom case 11A, a part of the air taken from the opening 8 is exhausted through the ventilation hole 12B penetrating the supporting section 12A from the opening 9 to the outside.

Figure 5:
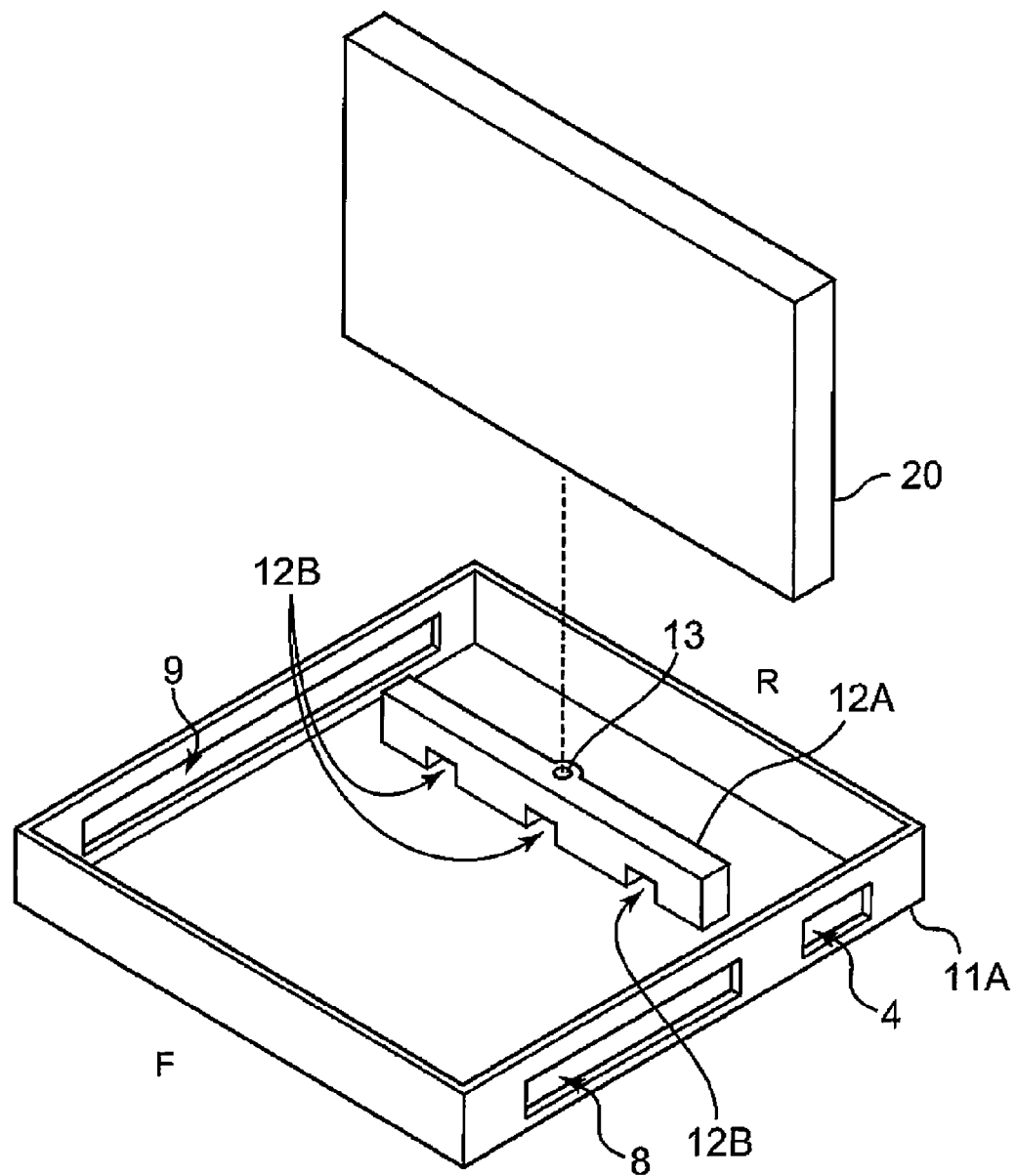
FIG. 5 is a perspective view showing a variation example of the second embodiment.
Figure 6:
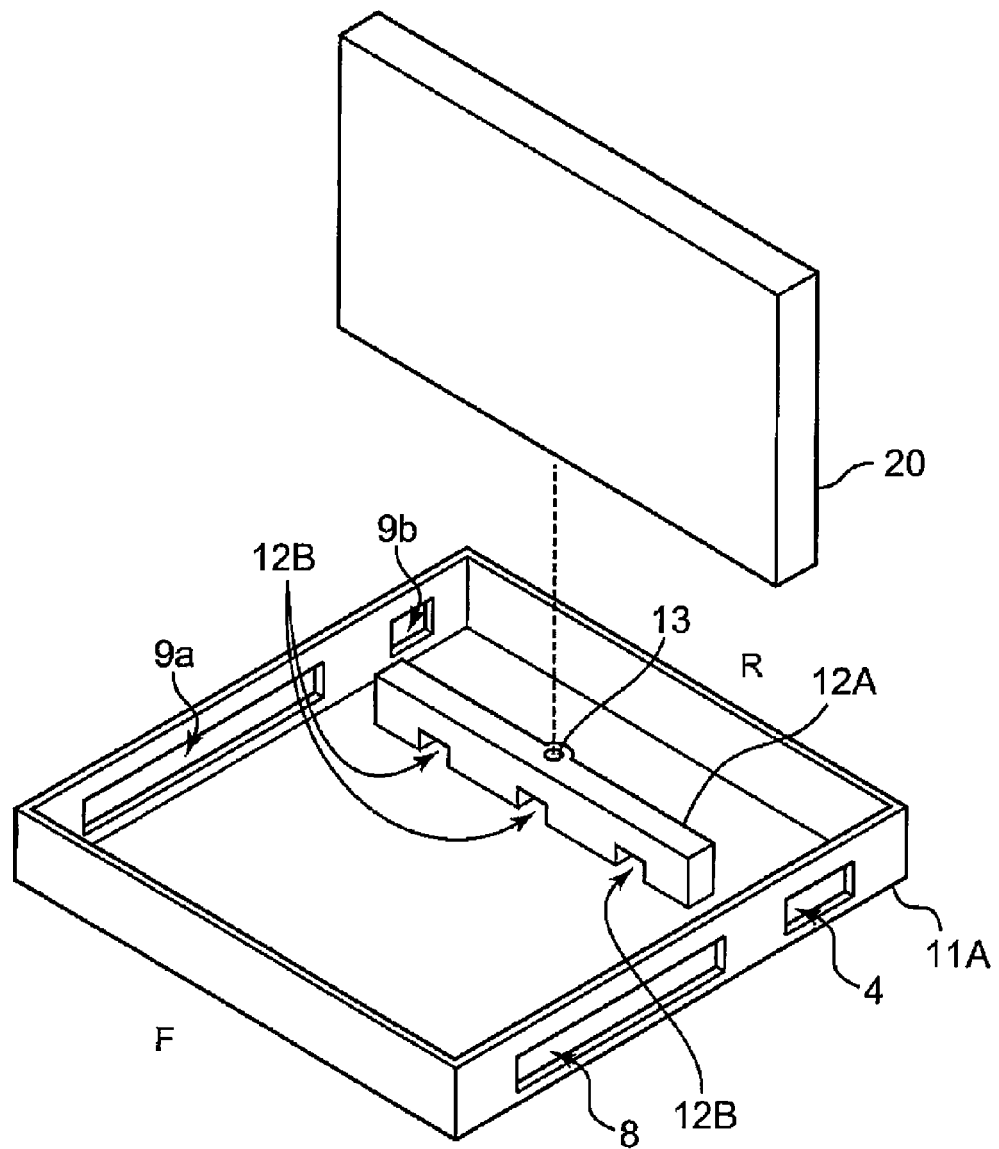
FIG. 6 is a perspective view showing a further variation example of the example shown in FIG. 5.

FIG. 5 shows the variation example in the second embodiment shown in FIG. 4. Then, the difference from FIG. 4 lies in a configuration in which the board and the resin plate are not placed inside the opening 4 and then the opening 4 is used as an air intake port. FIG. 6 shows the further variation example in the example shown in FIG. 5. Then, the difference from FIG. 5 lies in a configuration in which the single large opening 9 in FIG. 5 is divided into two openings 9a, 9b.

Figure 14:
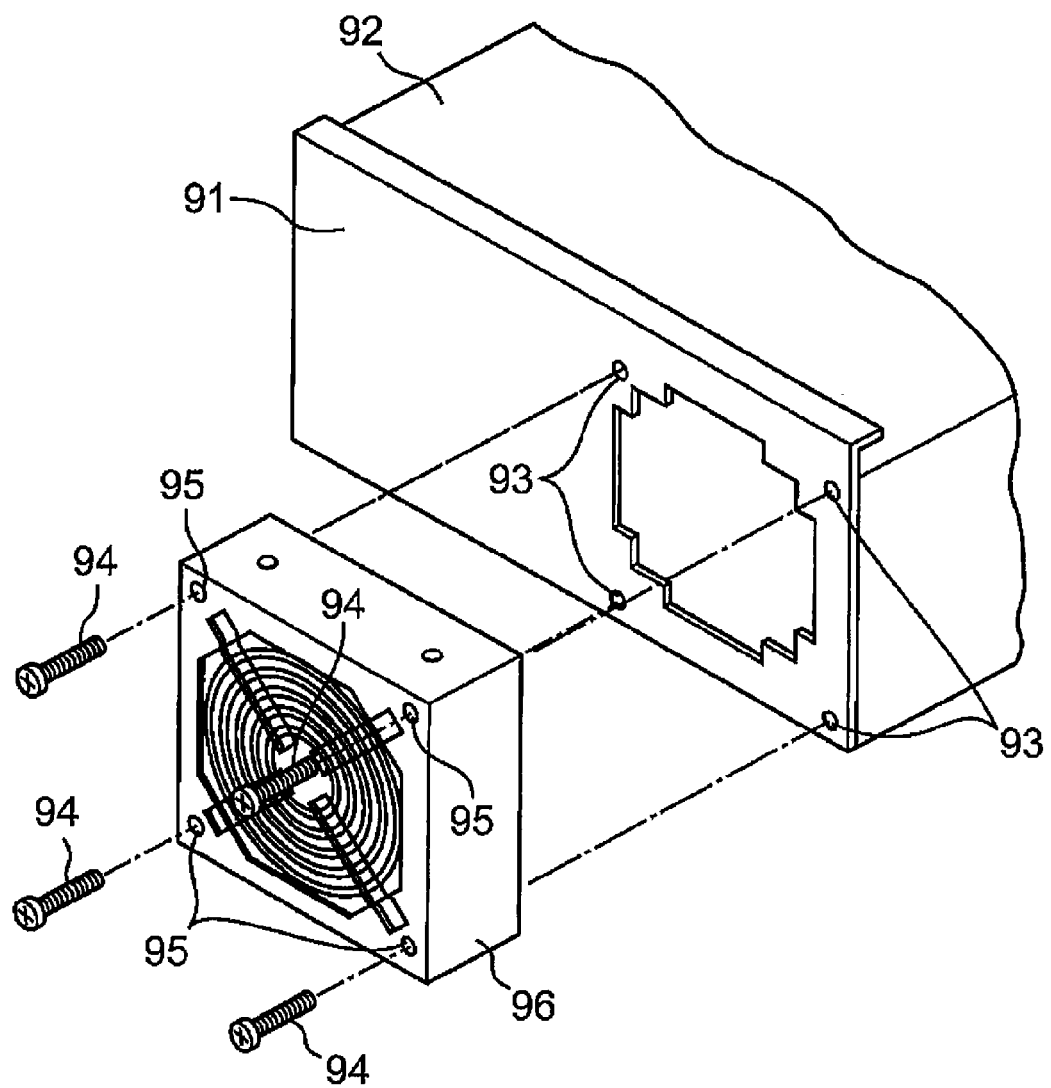
FIG. 14 is an exploded perspective view showing a method of attaching the cooling fan to the main body in the conventional ultrasonic diagnosis apparatus.

As the third embodiment to sixth embodiment of the ultrasonic diagnosis apparatus according to the present invention, a method of attaching the cooling fan to the main body or bottom case will be described below. Prior to its description, the conventional cooling fan attaching method is described with reference to FIG. 14. In the portable or laptop ultrasonic diagnosis apparatus, the space in which the structure to attach the necessary connector, switch or cooling fan for the thermal exhaustion is installed is limited and narrow, as compared with the ultrasonic diagnosis apparatus of a platform type. For this reason, the attachment portions of those sections are concentrated in the rear side of the main body and the attachment surface end. Thus, in the conventional electric product, when a member 96 arranged on the attachment surface end of the connector, the switch or the cooling fan for the thermal exhaustion as shown in FIG. 14 or the like is attached, screw holes 93, 95 are formed on the member 96 arranged in the attachment surface end and the lower portion of a panel 91 in an ultrasonic diagnosis apparatus 92. Then, the member 96 arranged on the side is configured to be laterally attached to the panel 91 in the ultrasonic diagnosis apparatus 92, by using screws 94 (for example, refer to Japanese Laid Open Patent Application (JP-A-Heisei, 5-121886).

However, in this configuration, an attaching worker must carry out a work while checking the screw holes on the lower portion of the rear panel. So, the attaching work cannot be carried out unless the attaching worker makes an unreasonable pose, such as a squatting pose and the like, in order to fixing them by using a driver and the like. Moreover, since the wiring of the member to be arranged on the attachment surface end is attached under the unreasonable pose, there is a case that even the wiring is disconnected, or the wiring is tangled. Thus, since a workbench or a desk is placed, a wide working space is required. Moreover, when the ultrasonic diagnosis apparatus is required to be repaired, a hospital in which the ultrasonic diagnosis apparatus is installed does not have the sufficient working space, in many cases, and the repairing operation is required to be completed in a short time. Also, the attachment members to be arranged on the attachment surface ends are individually used. Thus, there is a problem that, when it is attached, correspondingly to the individual attachment member, one fixing standard member is required to fix it to the attachment surface end.

The third embodiment to sixth embodiment according to the present invention are intended to solve the above conventional problems and can provide the ultrasonic diagnosis apparatus in which the work in the narrow space can be carried out, and even the plurality of attachment members can be easily fixed to the attachment surface ends under the small number of the attachments, and the working efficiency can be improved.

In the third embodiment to sixth embodiment of the ultrasonic diagnosis apparatus according to the present invention, it contains: at least one attachment member to be arranged at the attachment surface end of the ultrasonic diagnosis apparatus; the collective member to integrate the attachment members; and the fixing member to attach the collective member to the attachment surface end, and has the configuration that can be attached toward the attachment surface from above, by means of the fixing member.

With this configuration, the attachment position becomes clear, and the parts can be easily assembled and attached by means of the collective member. Thus, the work becomes easy, and the assembling time is reduced.

Also, even when there are one or more side walls vertical to the attachment surface, the wiring is structured to be pulled from the upper direction of the attachment member. Thus, the work becomes easy.

According to the third embodiment to sixth embodiment of the ultrasonic diagnosis apparatus according to the present invention, it contains: at least one attachment member to be arranged at the attachment surface end of the ultrasonic diagnosis apparatus; the collective member to integrate the attachment members; and the fixing member to attach the collective member to the attachment surface end, and the attaching action can be carried out toward the attachment surface from above, by means of the fixing member. As the effect resulting from being able to be attached from above, the attachment position becomes clear, and the parts can be easily assembled and attached by means of the collective member. Thus, the work becomes easy, and the working time is reduced. Also, since the attachment members are collected by means of the collective member, the attachment portions at which they are fixed to the attachment surfaces can be minimized. Hence, as compared with the number of the attachment members arranged at the attachment surface ends, the number when they are fixed to the attachment surfaces is small. Also, the unreasonable pose of the worker is released, which leads to the improvement of the assembling productivity and the reduction in the assembling time.

Moreover, the members can be collected and the attachment portions at which they are fixed to the attachment surfaces can be minimized, which can miniaturize the apparatus. Also, the worker can carry out the work from above the apparatus. Thus, since the work can be carried out in the narrow portion, such as the surface on the desk in a consultation room in a hospital and the like, the work can be carried out inside the limited space inside the hospital. Also, the user who purchases the apparatus can attain the reduction in a maintenance time and the increase in the number of the patients per day, and can carry out the work in the limited space, such as the surface on the desk in the consultation room and the like. Hence, the ultrasonic diagnosis apparatus that can minimize the burden on the usual task can be provided.

The third embodiment to sixth embodiment of the ultrasonic diagnosis apparatus according to the present invention will be described below with reference to FIG. 7 to FIG. 11. The feature of the third embodiment to sixth embodiment lies in the structure in which the cooling fan is attached to the main body or bottom case of the ultrasonic diagnosis apparatus or its bottom surface.

Third Embodiment

Figure 7:
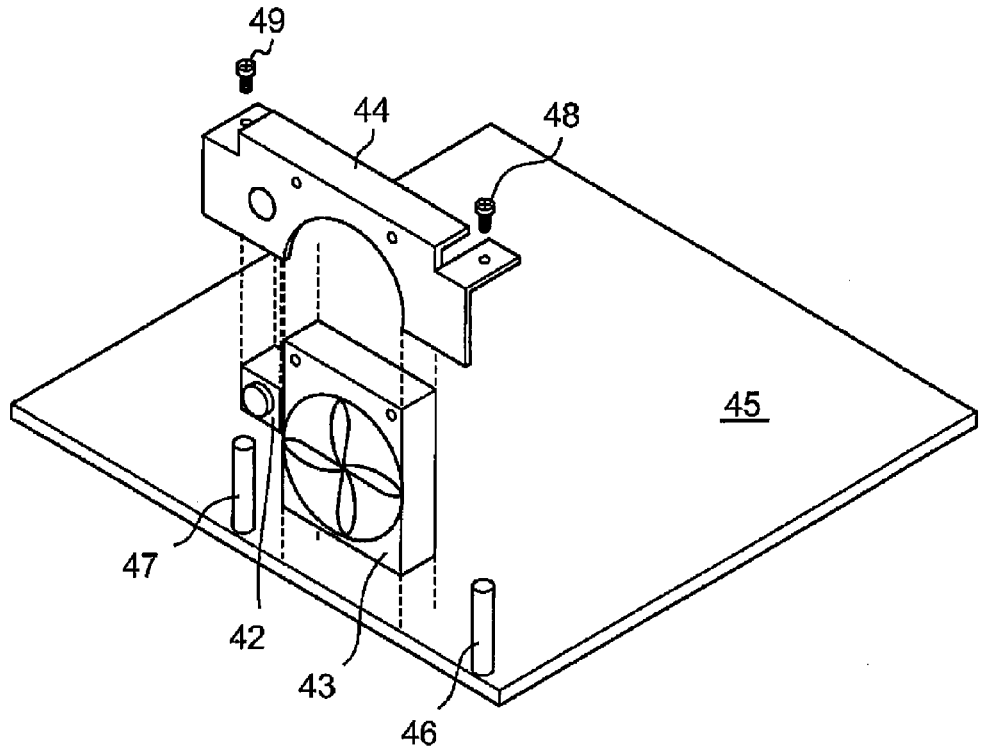
FIG. 7 is an exploded perspective view showing a manner in which a cooling fan is attached to a main body in a third embodiment of the ultrasonic diagnosis apparatus according to the present invention.
Figure 8:
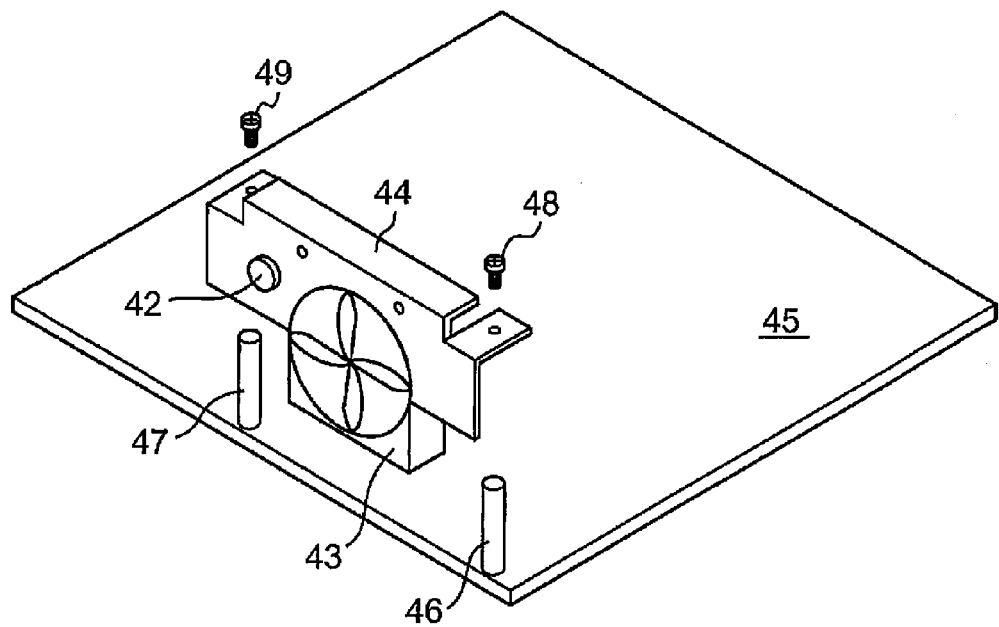
FIG. 8 is an exploded perspective view showing a manner in which a switch and the cooling fan shown in FIG. 7 are attached to a collective attachment member.

FIG. 7 is the exploded perspective view showing the manner in which the cooling fan is attached to the main body in the third embodiment of the ultrasonic diagnosis apparatus according to the present invention, and the view showing the manner in which the cooling fan and the like are attached to the bottom surface (base section) of the main body, namely, an attachment surface 45 that is the bottom surface of the bottom case. When in FIG. 7, a switch 42 and a cooling fan 43 that are the attachment members are attached to a collective attachment member 44, they are as shown in FIG. 8. That is, FIG. 8 shows the manner in which the switch and the cooling fan shown in FIG. 7 are attached to the collective attachment member. The attachment surface 45 of the base section contains supporting bars 46, 47 and serves as the base to which the collective attachment member 44 is attached. Screws 48, 49 serving as fixing materials are intended to attach the collective attachment member 44 to the supporting bars 46, 47.

As for the above configuration, the attaching method will be described below. At first, the switch 42 and the cooling fan 43 that are the attachment members are fixed to the collective attachment member 44 through the screws or adhesive agent serving as the fixing member, and then integrated. Next, the integrated collective attachment member 44 is attached to the supporting bars 46, 47 through the screws 48, 49 serving as the fixing members. In the third embodiment, the switch 42 and the cooling fan 43 that are the attachment members can be attached to the base section attachment surface 45 by using the two screws 48, 49, from above, by the standing user, in the narrow space. Thus, the number of the attachment members and the number of the fixing members can be made equal. With regard to this number of the fixing members, the two fixing members can be used to fix them to the attachment surface 45, even if the number of the attachment members is increased. Thus, the small number of the fixing members can be used to fix them. As compared with the case in which the attachment members are individually attached, the small number of the fixing members can be used to fix them to the attachment surface 45. Hence, the working efficiency can be made high from the viewpoint of a time.

In this way, the screws 48, 49 are attached from above, and even the plurality of attachment members can be easily fixed to the attachment surface ends by using the small number of the fixing members. Thus, the apparatus itself can be miniaturized, and the working efficiency can be made high, and the work in the narrow space can be carried out.

By the way, as the attachment members, there are a connector, an LED, a speaker and the like, in addition to the switch and the cooling fan.

Fourth Embodiment

Figure 9:
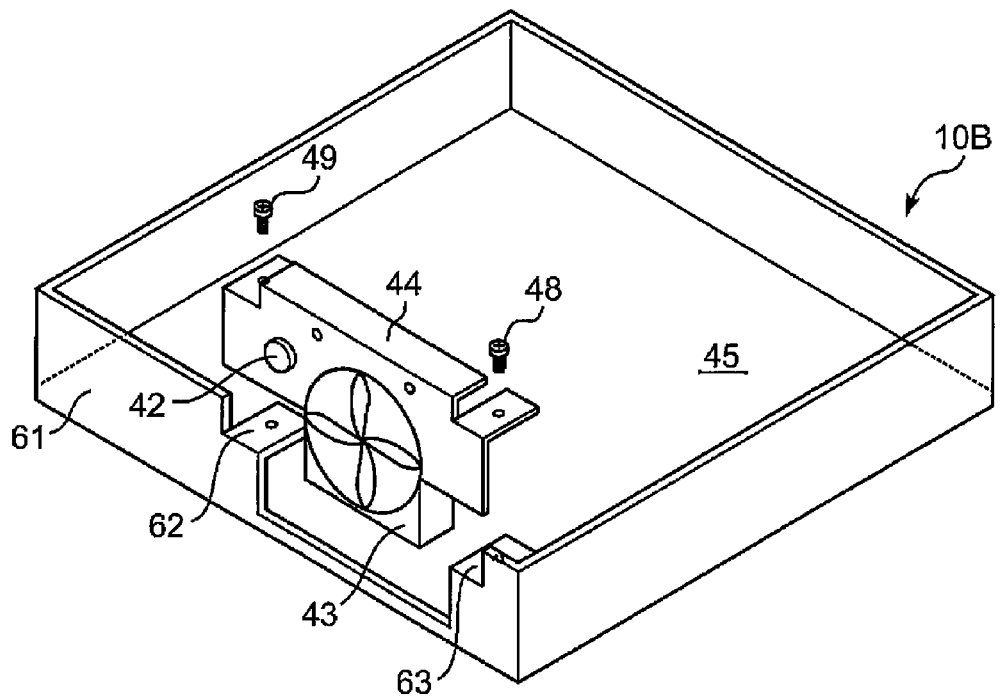
FIG. 9 is an exploded perspective view showing a manner in which the cooling fan is attached to a main body in a fourth embodiment in the ultrasonic diagnosis apparatus according to the present invention.

FIG. 9 is the exploded perspective view showing the manner in which the cooling fan is attached to the main body in the fourth embodiment in the ultrasonic diagnosis apparatus according to the present invention. In FIG. 9, a main body 10B has one or more side walls 61 vertical to the attachment surface 45 at the ends of the attachment surface 45 in the base section. Also, the supporting section is placed on the side wall 61, and this is the attachment section to which the collective attachment member 44 is attached. The screws 48, 49 serving as the fixing members are intended to attach the collective attachment member 44 to side installation supporting sections 62, 63.

As for the above configuration, the attaching method will be described below. At first, the switch 42 and the cooling fan 43 that are the attachment members are fixed to the collective attachment member 44 through the screws or adhesive agent or the like and then integrated. Next, the integrated collective attachment member is attached to the side installation supporting sections 62, 63 by using the screws 48, 49 serving as the fixing members. In the fourth embodiment, the switch 42 and the cooling fan 43 that are the attachment members can be attached to the attachment surface 45 through the two screws 48, 49, from above, by the standing user, in the narrow space. Thus, the number of the attachment members and the number of the fixing members can be made equal. With regard to this number of the fixing members, the two fixing members can be used to fix them to the attachment surface, even if the number of the attachment members is increased. Thus, the small number of the fixing members can be used to fix. As compared with the case in which the attachment members are individually attached, the small number of the fixing members can be used to fix. Hence, the working efficiency can be made high from the viewpoint of a time.

In this way, the screws 48, 49 are attached from above, and even the plurality of attachment members can be easily fixed to the side wall 61 by using the small number of the attachments. Thus, the apparatus itself can be miniaturized, and the working efficiency can be made high, and the work in the narrow space can be carried out.

Fifth Embodiment

Figure 10:
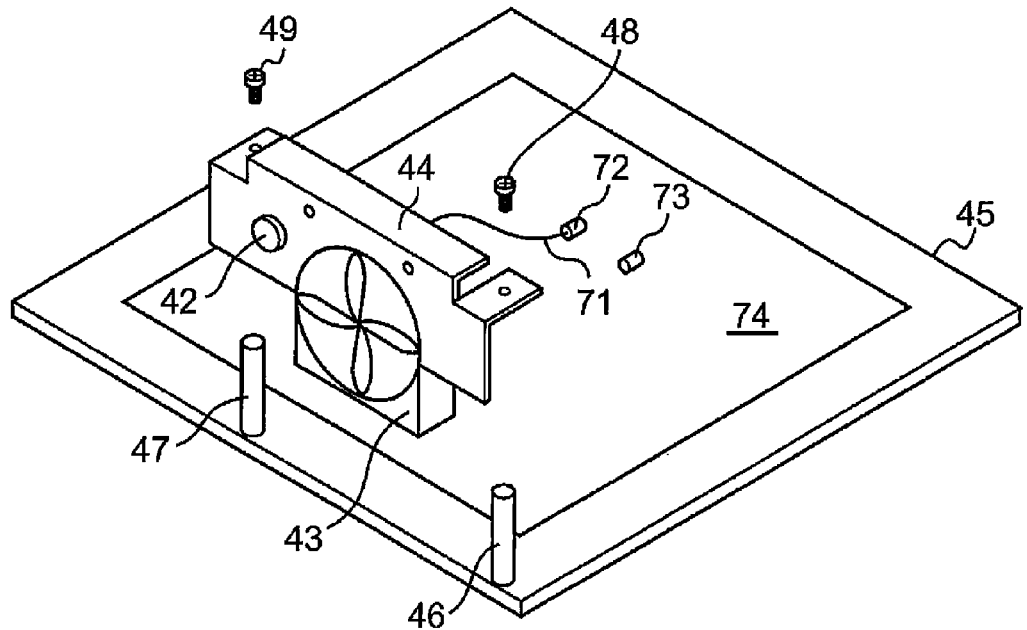
FIG. 10 is an exploded perspective view showing a manner in which the cooling fan is attached to a main body in a fifth embodiment in the ultrasonic diagnosis apparatus according to the present invention.

FIG. 10 is the exploded perspective view showing the manner in which the cooling fan is attached to the main body in the fifth embodiment in the ultrasonic diagnosis apparatus according to the present invention. In FIG. 10, a wiring 71 is pulled from the upper portion of the attachment member. Also, ahead of the wiring 71, there is a connected connector 72. This connector 72 is connected to a connector connection destination 73 arranged on a board 74 that is one of electrical parts assembled on the attachment surface 45 on the bottom surface of the main body (or the bottom case of the main body) in the ultrasonic diagnosis apparatus.

The above configuration, the attaching method will be described below. At first, as described in the third embodiment and the fourth embodiment, the collective attachment member 44 is fixed to the supporting bars 46, 47. After that, the connector 72 of the wiring 71 pulled from the upper direction of the switch 42 and the cooling fan 43 that are the attachment members is connected to the connector connection destination 73 located on the board 74 that is one of the electric parts assembled on the attachment surface 45 in an ultrasonic diagnosis apparatus 41. In this way, since the wiring is pulled from the upper direction, the wiring situation can be easily known, and the connection situation can be also easily known. Thus, the trouble that the wiring is tangled is reduced, which can reduce an erroneous action.

Sixth Embodiment

Figure 11:
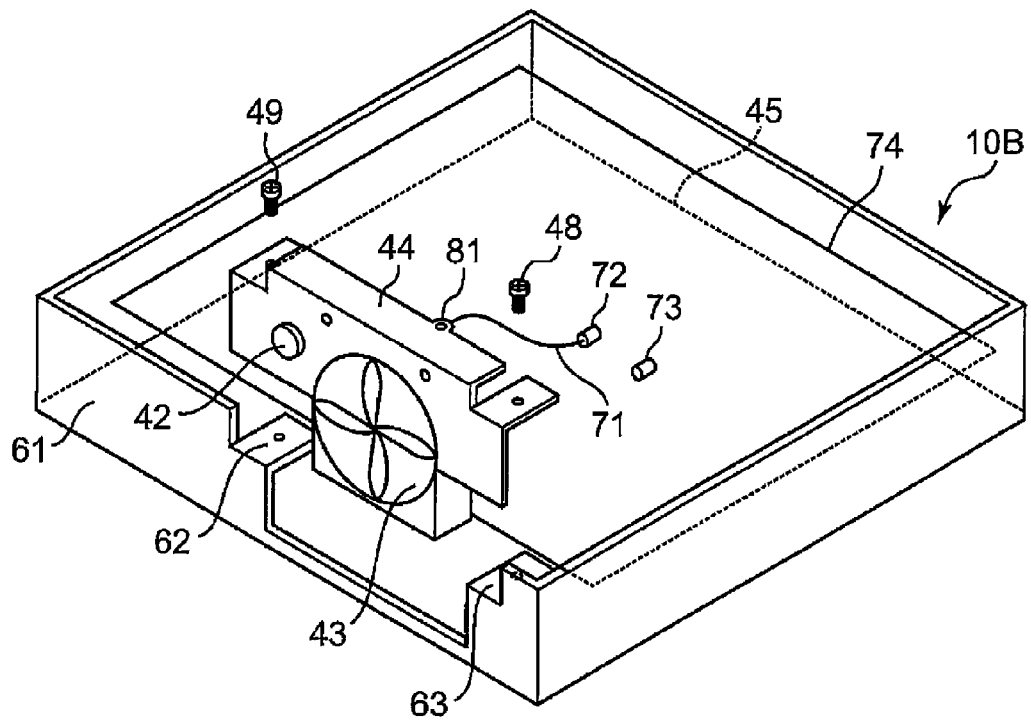
FIG. 11 is an exploded perspective view showing a manner in which the cooling fan is attached to a main body in a sixth embodiment in the ultrasonic diagnosis apparatus according to the present invention.
Figure 12:
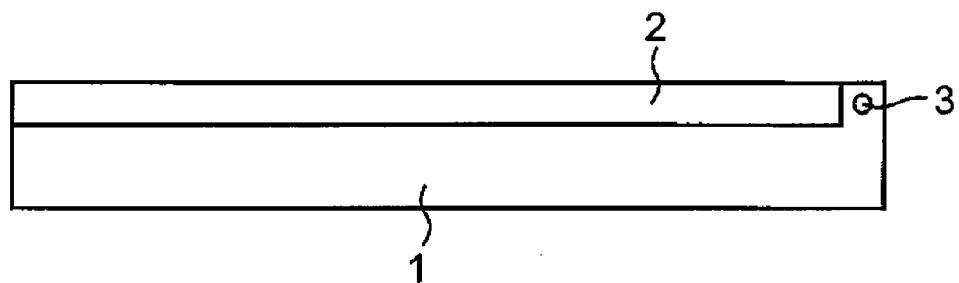
FIG. 12 is a view showing a subject to be solved by the present invention, and a right side view showing the conventional portable ultrasonic diagnosis apparatus in a situation in which the display section is closed.
Figure 13:
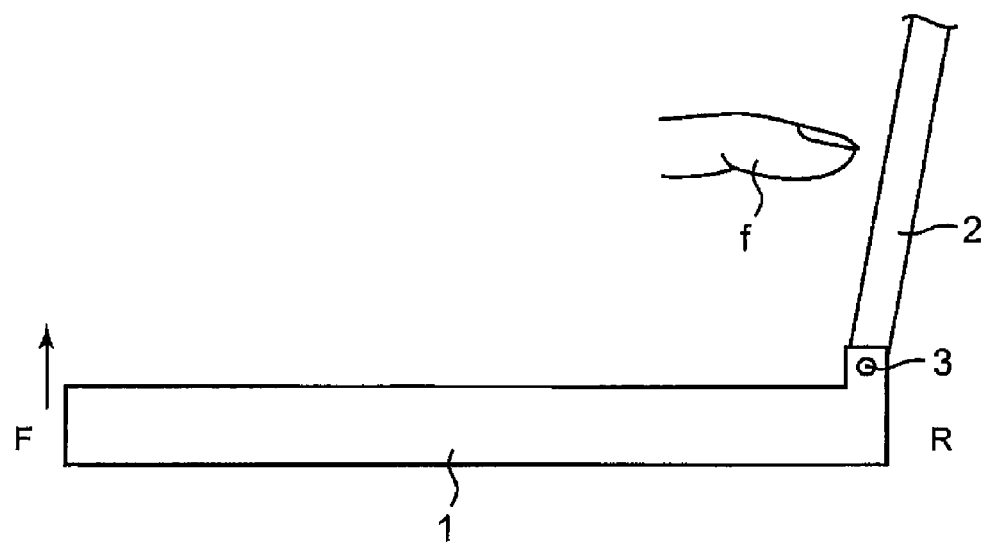
FIG. 13 is a view showing a subject to be solved by the present invention, and a right side view showing a manner in which the display section in the ultrasonic diagnosis apparatus shown in FIG. 12 is opened and a user operates a touch panel on a display section surface.

FIG. 11 is the exploded perspective view showing the manner in which the cooling fan is attached to the main body in the sixth embodiment in the ultrasonic diagnosis apparatus according to the present invention. In the sixth embodiment, instead of the supporting bars 46, 47 in the fifth embodiment, the side wall 61 and the side installation supporting sections 62, 63 similar to the fourth embodiment are further installed. The wiring 71 pulled from the upper portion of the switch 42 and the cooling fan 43 that are the attachment members is fixed not so as to be tangled, and a wiring stopper 81 is placed in order to make the working efficiency high. By the way, the wiring stopper can be placed even when the side wall 61 is not used.

As for the above configuration, the attaching method will be described below. At first, as described in the third embodiment and the fourth embodiment, the collective attachment member 44 is fixed to the attachment surface 45. After that, the wiring 71 pulled from the upper direction of the switch 42 and the cooling fan 43 that are the attachment members is fixed by the wiring stopper 81 in the collective member 44. Then, the connector 32 of the wiring 71 is connected to the connector connection destination 73 located on the board 74 that is one of the electric parts assembled on the main body 10B in the ultrasonic diagnosis apparatus or the base section of the bottom case thereof. In this way, since the wiring is pulled from the upper portion, the wiring situation can be easily known, and the connection situation can be also easily known. Moreover, since the wiring 71 is fixed by the wiring stopper 81 located on the collective member 44, the movement of the wiring 71 is suppressed, thereby stabilizing it. Also, the trouble that the wiring is tangled is reduced, and the erroneous action can be reduced, which can make the working efficiency high.

As can be evident from the above description, according to the third embodiment to sixth embodiment according to the present invention, it contains: at least one attachment member to be arranged at the attachment surface end of the ultrasonic diagnosis apparatus; the collective member to integrate the attachment members; and the fixing member to attach the collective member to the attachment surface end, and the attaching action can be carried out toward the attachment surface from above, by means of the fixing member. As the effect of the attaching action from above, the attachment position becomes clear, and the parts can be easily assembled and attached by using the collective member. Thus, the work is easy, and the time is reduced. Also, since the attachment members are collected by using the collective member, the attachment portions at which they are fixed to the attachment surfaces can be minimized. Hence, as compared with the number of the attachment members arranged at the attachment surface ends, the number when they are fixed to the attachment surfaces becomes small. Also, according to the third embodiment to sixth embodiment according to the present invention, the unreasonable pose of the worker is released, which leads to the improvement of the assembling productivity and the reduction in the assembling time.

Moreover, according to the third embodiment to sixth embodiment according to the present invention, the members can be collected and the attachment portions at which they are fixed to the attachment surfaces can be minimized, which can miniaturize the apparatus. Also, since the work can be carried out from above, the work can be carried out in the narrow portion, such as the surface on the desk in the consultation room in the hospital and the like. Thus, the work can be carried out inside the limited space inside the hospital. Also, the user who purchases the apparatus can attain the reduction in the maintenance time and the increase in the number of the patients per day, and can carry out the work in the limited space, such as the surface on the desk in the consultation room and the like. Hence, it is possible to provide the ultrasonic diagnosis apparatus that can minimize the burden on the daily task.

INDUSTRIAL APPLICABILITY

In the present invention, in the configuration in which the display section having the touch panel is opened/closed with respect to the main body, it optimizes the position of the hinge mechanism for connecting the display section and the main body and the strength of the main body and also has the effect of being able to reduce the noise from the various parts, such as the power source, the CPU board and the like, on the ultrasonic image processing circuit board arranged inside the main body, and it can be used in the ultrasonic diagnosis apparatus and the like.

The invention claimed is:

1. An ultrasonic diagnosis apparatus comprising:
    an apparatus main body:
    a display section, which can be opened/closed with respect to said apparatus main body;
    a supporting section that is placed inside said apparatus main body and openably/closably supports said display section and extends up to a bottom surface of said apparatus main body, the supporting section dividing an inner space of said apparatus main body into a plurality of regions which include a first region and a second region;
    a first circuit section that is installed in said first region inside said apparatus main body and includes an image processing circuit; and
    a second circuit section that is installed in said second region inside said apparatus main body and includes a circuit of a function different from said image process.

2. The ultrasonic diagnosis apparatus according to claim 1, wherein said supporting section is formed to stand upright and extend in a width direction of said apparatus main body, on the bottom surface of said apparatus main body of a position that is dislocated to a front end side from a rear end of said apparatus main body.

3. The ultrasonic diagnosis apparatus according to claim 1, wherein said supporting section has a vertical shaft serving as a rotation shaft that enables said display section to be rotated in a horizontal direction with respect to said apparatus main body and a horizontal shaft serving as an opening/closing shaft that enables it to be opened/closed in an upper/lower direction.

4. The ultrasonic diagnosis apparatus according to claim 1, wherein said supporting section is a 2-shaft hinge mechanism that has said vertical shaft and said horizontal shaft.

5. The ultrasonic diagnosis apparatus according to claim 2, wherein said first region is placed in a region on a main body front end side from said supporting section,
    said second region is placed in a region on a main body rear end side from said supporting section, and
    a CPU and a power source unit are arranged in said second region.

6. The ultrasonic diagnosis apparatus according to claim 2, wherein a distance between a front end of the apparatus main body and said supporting section is longer than a distance between said rear end of the apparatus main body and said supporting section.

\* \* \* \* \*